(12) United States Patent
Srivari et al.

(10) Patent No.: US 10,752,585 B2
(45) Date of Patent: Aug. 25, 2020

(54) PROCESS FOR THE PREPARATION OF ZAFIRLUKAST AND ANALOGS THEREOF

(71) Applicant: Council of Scientific & Industrial Research, New Delhi (IN)

(72) Inventors: Chandrasekhar Srivari, Telangana (IN); Prathama Satyendra Mainkar, Telangana (IN); Srinu Paladugu, Telangana (IN); Pavan Kumar Togapur, Telangana (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 16/646,462

(22) PCT Filed: Aug. 6, 2018

(86) PCT No.: PCT/IN2018/050513
§ 371 (c)(1),
(2) Date: Mar. 11, 2020

(87) PCT Pub. No.: WO2019/130334
PCT Pub. Date: Jul. 4, 2019

(65) Prior Publication Data
US 2020/0216390 A1 Jul. 9, 2020

(30) Foreign Application Priority Data
Dec. 28, 2017 (IN) .............................. 201711046976

(51) Int. Cl.
*C07D 209/04* (2006.01)
(52) U.S. Cl.
CPC ................................. *C07D 209/04* (2013.01)
(58) Field of Classification Search
CPC .................................................. C07D 209/04
See application file for complete search history.

(56) References Cited

U.S. PATENT DOCUMENTS

| | | | |
|---|---|---|---|
| 4,859,692 | A | 8/1989 | Bernstein et al. |
| 5,319,097 | A | 6/1994 | Holohan et al. |
| 5,993,859 | A | 11/1999 | Timko et al. |
| 2009/0149662 | A1 | 6/2009 | Anumula et al. |

FOREIGN PATENT DOCUMENTS

| | | |
|---|---|---|
| CN | 101104601 A | 1/2008 |
| CN | 102199117 A | 9/2011 |
| CN | 103396353 A | 11/2013 |
| CN | 105367478 A | 3/2016 |
| EP | 0199543 A2 | 10/1986 |
| WO | 2002046153 A2 | 6/2002 |
| WO | WO-2019130334 A1 * | 7/2019 ............ C07D 209/24 |

OTHER PUBLICATIONS

Goverdhan et al.; "An Improved and Scalable Process for Zafirlukast: An Asthma Drug", Organic Process Research & Development, (2009), 13: pp. 67-72.
Jana et al.; "Visible-light-induced oxidant and metal-free dehydrogenative cascade trifluoromethylation and oxidation of 1, 6-enynes with water", Chemical Science (2017), 8: pp. 6633-6644.
Xiao-Feng Xia et al.; "Palladium—copper-cocatalyzed intramolecular oxidative coupling; an efficient and atom- economical strategy for the synthesis of 3-acylindoles", Chemical Communications, (2013), 49: pp. 1410-1412.
Ping Zhang et al.; "Synthesis of 3-Acylindoles by Visible-Light Induced Intramolecular Oxidative Cyclization of o-Alkynylated N,N-Dialkylamines", Organic Letters, (2014), 16: pp. 3264-3267.
Gampe et al.; "Arynes and Cyclohexyne in Natural Product Synthesis", Agnew, Chem. In. Ed, (2012), 51: pp. 3766-3778.
Wu et al.; "Mild and Selective Ru-Catalyzed Formylation and Fe-Catalyzed Acylation of Free (N-H) Indoles Using Anilines as the Carbonyl Source", J Am. Soc., (2011), 133: 11924-11927.
Gogoi et al.; "A metal free domino synthesis of 3-aroylindoles via two sp3 C-H activation", Chem. Commun., (2014), 50: 104445-10447.
Gogoi et al.; "A Copper-Catalyzed Synthesis of 3-Aroylindoles via a sp3 C-H Bond Activation Followed by C-C and C-O Bond Formation"; Org. Lett., (2013), 15: 1802 A-D.
Gabriele et al.: "A General Synthesis of Indole-3-carboxylic Esters by Palladium-Catalyzed Direct Oxidative Carbonylation of 2-Alkynylaniline Derivatives", Eur. J. Org. Chem., (2012), 2549-2559.
Bernini et al.; "Copper-Catalyzed C-C Bond Formation through C-H Functionalization: Synthesis of Multisubstituted Indoles from N-Aryl Enaminones", Angew. Chem, Int. Ed., (2009), 48: 8078-8081.
Xia et al; "Palladium—copper-cocatalyzed intramolecular oxidative coupling: an efficient and atom-economical strategy for the synthesis of 3-acylindoles", Chem. Commun., (2013), 49: 1410-1412.
Matassa et al.; "Evolution of a Series of Peptidoleukotriene Antagonists: Synthesis and Structure/Activity Relationships of 1,3,5,-Substituted Indoles and Indazoles"; J. Med. Chem., (1990), 33: 1781-1790.
Llinas et al.; "Two new Polymorphic cocrystals of Zafirlukast: Preparation, Crystal Structure, and Stability Relations"; Q. Cryst. Growth Des., (2015), 15: 4162.
Bharathi et al.; "Development and validation of a sensitive LC-MS/MS method with electrospray ionization for quantitation of zafirlukast, a selective leukotriene antagonist in human plasma: application to a clinical pharmacokinetic study"; Biomed. Chromatogr.; 22: (2008), 645-653.

* cited by examiner

*Primary Examiner* — Sun Jae Yoo
(74) *Attorney, Agent, or Firm* — Dilworth & Barrese, LLP

(57) ABSTRACT

The present invention relates to a process for the preparation of (1-alkylindol-3-ylmethyl) benzoic acid derivatives, in particular Zafirlukast and analogs thereof. Further, this process is based on protection group free and C—H bond activation strategy involving all step catalytic transformation sequence and comprises the following steps: Sonogashira coupling, indole formation by Sp³ C—H activation, reductive hydrogenation and amidation.

10 Claims, 3 Drawing Sheets

PROCESS FOR THE PREPARATION OF ZAFIRLUKAST AND ANALOGS THEREOF

FIELD OF THE INVENTION

The present invention relates to a process for the preparation of (1-alkylindol-3-ylmethyl) benzoic acid derivatives, in particular Zafirlukast and analogs by catalytic C—H activation method thereof.

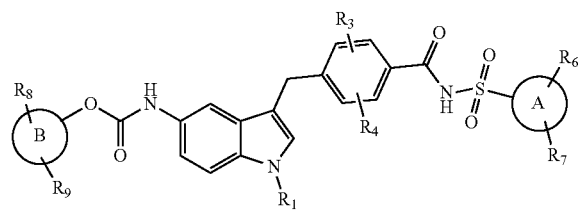

wherein
ring A and B is comprising aryl, heteroaryl, cycloalkyl, fused aryl, fused alkyl or fused heteroaryl; R1 is C1-C6 alkyl; $R_3$, $R_4$, $R_6$, $R_7$, $R_8$, $R_9$ is C1-12 alkyl, aryl, heteroaryl, C1-C12 cycloalkyl, heteroalkyl, thiol, H, —OR where R=H, C1-C6 alkyl, aryl or heteroaryl, $NO_2$, halogen, RNH where R=H, C1-C6 alkyl, aryl or heteroaryl; cyano, isothiocyano, isocyanate, azido, —COOR where R=H, C1-C6 alkyl, aryl or heteroaryl; —COR where R=H, C1-C6 alkyl, aryl or heteroaryl; wherein each of these groups may further be substituted with one or more substituents selected from H, OH, SH, halogen, CN, $NO_2$, C1-C4 alkyl or phenyl.

BACKGROUND OF THE INVENTION

Substituted indoles play a pivotal role in drug discovery, culminating in launch of several drugs including many molecules in clinical pipeline. The discovery and development of drugs to treat allergic conditions and asthma have attracted great importance in pharmaceutical industry. The success rate in this area of research has been significant because, the human intralobar airways have a single receptor for peptido leukotrienes. There has been a great progress reported in identifying selective peptide leukotriene antagonists. Indole and indazole compounds have been extensively investigated as selective antagonists of the leukotriene pathway. All these efforts have culminated in launching Zafirlukast as the oral leukotriene receptor antagonist (LTRA) for the maintenance treatment of asthma, prescribed in combination with bronchodilators and steroids. Some other marketed products with indole skeleton are panabinostat, oxindole, tropisetron etc.

Traditionally, these classes of compounds are synthesized from prefabricated indole which offers lesser flexibility in substitutions in the benzene ring of indole. Thus, a non-conventional strategy with formation of indole as the key step was the target of this preparation process. Therefore, the process for preparation of Zafirlukast starts with the construction of 3-aroylindoles, followed by further process steps to obtain the Zafirlukast and corresponding analogs library. There are several methods reported in the literature for the formation of indole moiety, which are generally carried out using transition metal catalysts. Some of these references are: (a) Eur. J. Org. Chem. 2012, 2549; (b) Angew. Chem. Int. Ed. 2012, 51, 3766; (c) J. Am. Chem. Soc. 2011, 133, 11924; (d) Angew. Chem. Int. Ed. 2009, 48, 8078; (e) Org. Lett. 2013, 15. 1802; (f) Chem. Commun. 2014, 50, 10445; (g) Chem. Commun. 2013, 49, 1410. However, there are no process methods which are based on peroxide free and transition metal-free cyclization protocol for indole formation. Till date, several procedures on the synthesis and applications for the Zafirlukast and related compounds/intermediates are reported in literature with varying levels of success and some of them are (a) U.S. Pat. No. 4,859,692; (b) U.S. Pat. No. 5,319,097; (c) U.S. Pat. No. 5,993,859; (d) WO2002046153; (e) EP0199543; (f) GB8509882; (g) GB8525658; (h) IN2899/CHE/2007; (i) US20090149662; (j) J. Med. Chem, 33, 1990, 1781; (k) CN105367478; (l) CN103396353; (m) CN102199117; (n) CN101104601; (o) OPRD 2009, 13, 67; (p) Biomed. Chromatogr., 22, 2008; 645; (q) Cryst., Growth Des. 2015, 15, 4162. Though, several of these methods are practical at laboratory level, only few of them are useful at industrial production. Most of these reported methods are difficult to be practiced at the industrial production due to one or more of the following factors: (a) expensive reagents and/or raw materials (b) uneven temperature and/or reaction times (c) multi-step process (d) operationally difficult reaction conditions/parameters.

OBJECTIVE OF THE INVENTION

Main objective of the present invention is to provide an efficient catalytic process for the preparation of (1-alkylindol-3-ylmethyl) benzoic acid derivatives in particular Zafirlukast and analogs thereof.

Another objective of the present invention is to provide a process, which could be carried out by employing C—H bond activation protocol using intramolecular oxidative coupling with protection group free approach.

SUMMARY OF THE INVENTION

Figure 1:
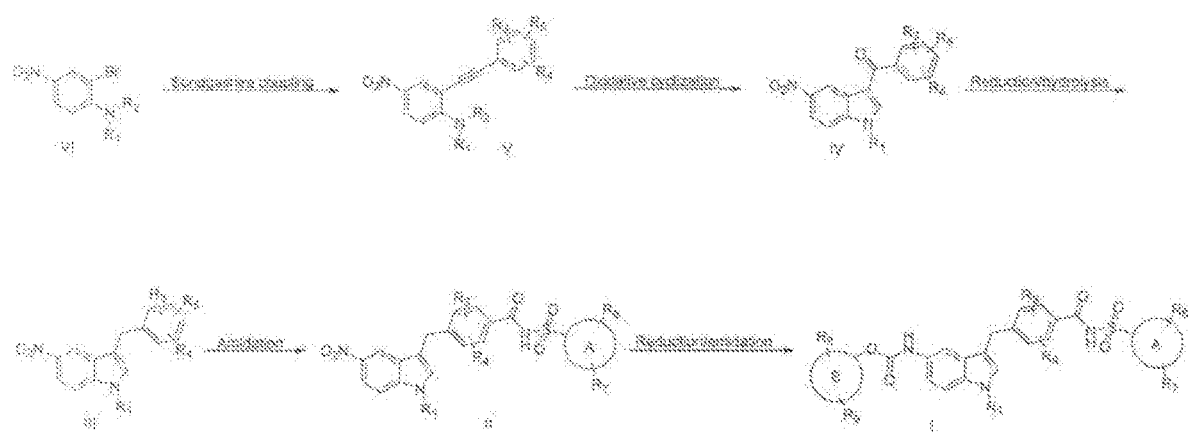
FIG. 1 represents the process steps for the preparation of (1-alkylindol-3-ylmethyl) benzoic acid derivatives, in particular Zafirlukast and analogs.
Figure 2:
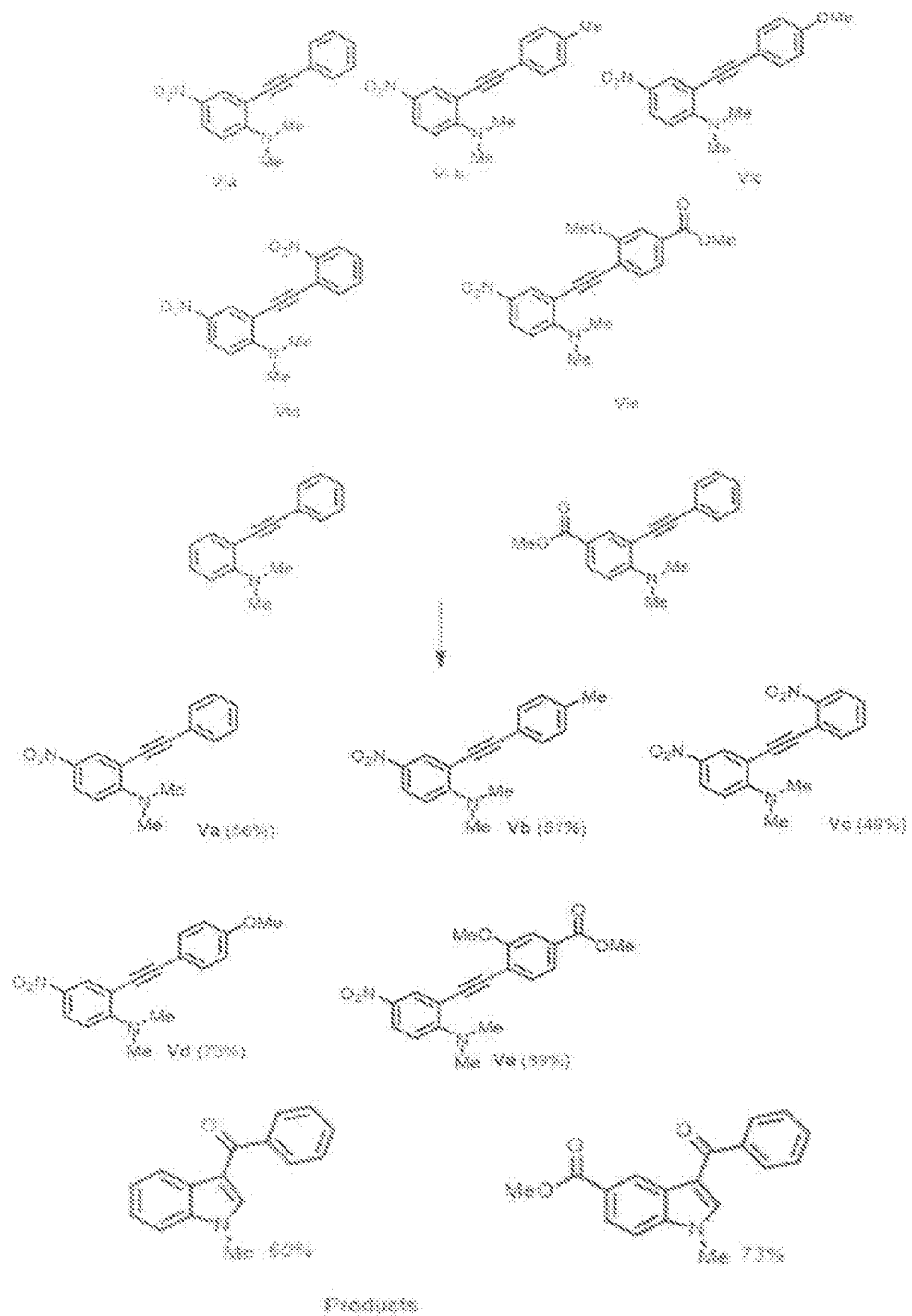
FIG. 2 represents the process for the preparation of compounds of formula V from the compounds of Formula VI.
Figure 3:
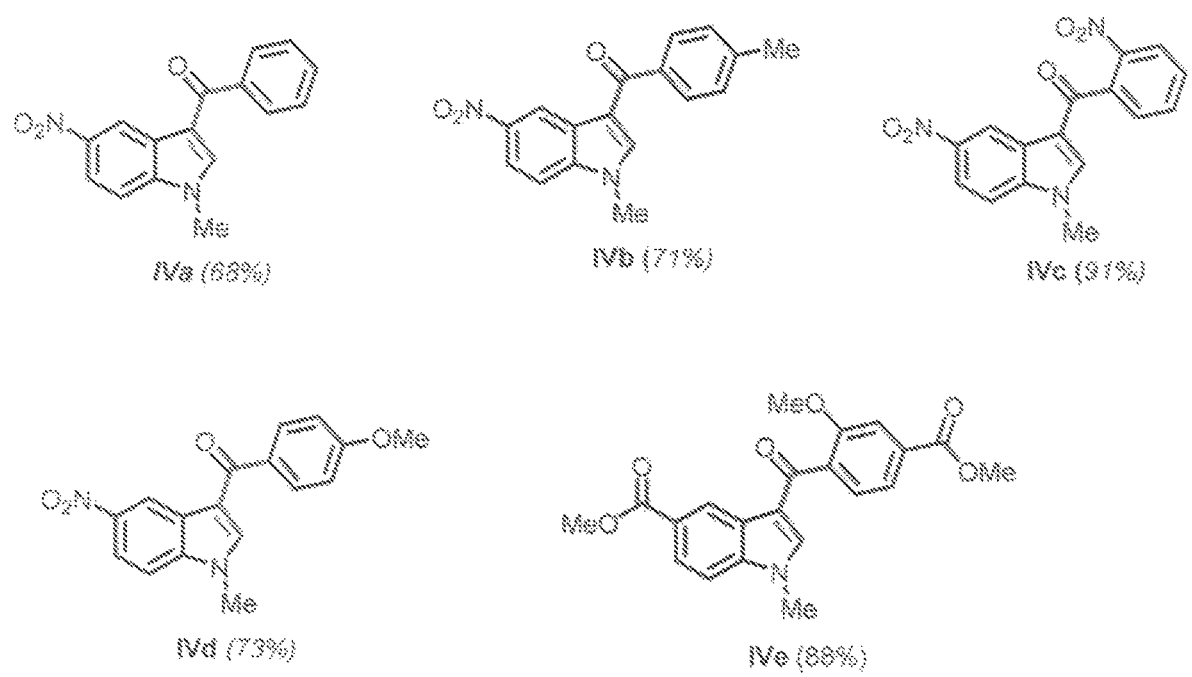
FIG. 3 represents compounds of formula IVa-e

Accordingly, present invention provides a process for the preparation of (1-alkylindol-3-ylmethyl) benzoic acid derivatives, in particular Zafirlukast and analogs compound of formula I, comprising the steps of:

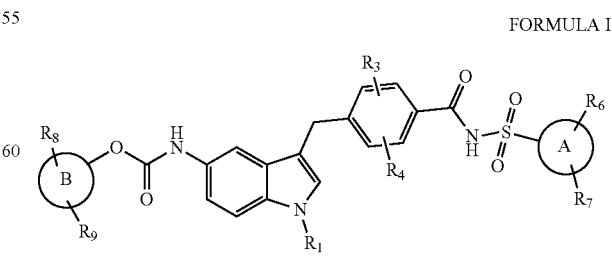

FORMULA I wherein ring A and B is any ring aryl, heteroaryl, cycloalkyl, fused aryl, fused alkyl or fused heteroaryl; $R_1$, $R_2$ is C1-C6 alkyl; $R_3$, $R_4$, $R_5$, $R_6$, $R_7$, $R_8$, $R_9$ is C1-12 alkyl, aryl, heteroaryl, C1-C12 cycloalkyl, heteroalkyl, thiol, H, —OR where R=H, C1-C6 alkyl, aryl or heteroaryl, $NO_2$, halogen, RNH where R=H, C1-C6 alkyl, aryl or heteroaryl; cyano, isothiocyano, isocyanate, azido, —COOR where R=H, C1-C6 alkyl, aryl or heteroaryl; —COR where R=H, C1-C6 alkyl, aryl or heteroaryl; wherein each of these groups may further be substituted with one or more substituents selected from H, OH, SH, halogen, CN, $NO_2$, C1-C4 alkyl or phenyl; (a) Sonagashira coupling of aryl bromide compound of formula VI and aryl acetylene using palladium catalyst, copper catalyst, organic base and inorganic base in polar solvent at 70-120° C. for 5-15 hours to yield compound of formula V; (b) oxidative cyclization of compound of formula V obtained in step (a) by $Sp^3$ C—H activation using persulfate oxidizing agent in polar solvents at 70-120° C. for 2-10 hours to yield compound of formula IV; (c) reductive hydrogenation of compound of formula IV obtained in step (b) using catalytic hydrogenation reagent, followed by acid hydrolysis in alcoholic solvent at 25-35° C. for 2-10 hours to yield compound of formula III; (d) amidation of acid group of the compound of formula III obtained in step (c) with sulfonamide using transition metal catalyst and anhydride in polar solvent at 25-35° C. for 1-5 hours to yield compound of formula II; (e) reduction of nitro group of the compound of formula II obtained in step (d) using catalytic reducing reagent in polar solvent at 25-35° C. for 1-5 hours, followed by amidation with haloformate using organic base in nonpolar solvent at 25-35° C. for 2-8 hours to obtain the desired compound of formula I.

In an embodiment of the present invention, the palladium catalyst is selected from palladium acetate, palladium chloride, tetrakis(triphenylphosphine)palladium(0), bis(triphenylphosphine)palladium(II) chloride, palladium (II) trifluoroacetate, diacetobis(triphenylphosphine)palladium(II), bis [(diphosphanyl)methyl]laminepalladium(II) dichloride, bis [(diphenylphosphanyl)methyl] aminepalladium(II)diacetate, 1,1'-Bis(diphenylphosphino)ferrocene] dichloropalladium (II), [1,1'-Bis(di-tert-butylphosphino)ferrocene] dichloropalladium(II) or mixtures thereof.

In yet another embodiment of the present invention, the aryl acetylene is selected from

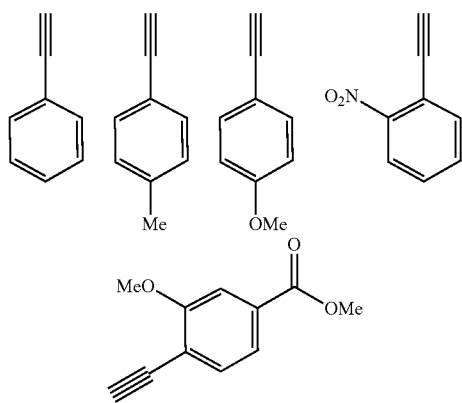

In yet another embodiment of the present invention, the copper catalyst is selected from copper iodide, copper bromide, copper chloride, copper acetate or mixtures thereof. In yet another embodiment of the present invention, the organic base is selected from secondary amine, tertiary amine or heterocyclic amine.

In yet another embodiment of the present invention, the inorganic base is selected from potassium carbonate, sodium carbonate, potassium bicarbonate, sodium bicarbonate, cesium carbonate, potassium phosphate, sodium phosphate or mixtures thereof. In yet another embodiment of the present invention, the polar solvent is selected from ethers, alcohols, halogenated solvents, esters, dimethylformamide, dimethylsulfoxide, acetonitrile or mixtures thereof.

In yet another embodiment of the present invention, the non-polar solvent is selected from toluene, hexane, benzene, pentane, heptane, xylene, mesitylene or mixtures thereof. In yet another embodiment of the present invention, the persulfate is selected from sodium persulfate, potassium persulfate or ammonium persulfate.

In yet another embodiment of the present invention, the catalytic hydrogenation reagent is selected from palladium on carbon or raney nickel.

In yet another embodiment of the present invention, the transition metal catalyst is selected from zinc chloride, zinc bromide, zinc iodide or titanium tetrachloride.

In yet another embodiment of the present invention, the anhydride is selected from benzoic anhydride, acetic anhydride, phthalic anhydride or maleic anhydride.

In still another embodiment of the present invention, the haloformate is selected from chloroformate, bromoformate or iodoformate.

In still another embodiment of the present invention, all the products are subjected to purification by chromatography, filtration, crystallization, distillation or extraction.

DETAILED DESCRIPTION OF THE INVENTION

Present invention provides a highly effective process for the preparation of (1-alkylindol-3-ylmethyl) benzoic acid derivatives, in particular Zafirlukast and analogs. Zafirlukast is an oral leukotriene receptor antagonist (LTRA) and an FDA approved drug for the treatment of asthma. The present process could be operated by employing all catalytic transformations to produce (1-alkylindol-3-ylmethyl) benzoic acid derivatives, in particular Zafirlukast and analogs in high yields and purity. This newly developed process starts from a one-pot three sequence reaction and comprises of the following operations: Sonogashira coupling, indole formation by $Sp^3$ C—H activation, reductive hydrogenation, amidation and reductive amidation as illustrated in scheme 1.

The present process can be performed very effectively in six overall steps with a short reaction time and is a highly viable strategy which could be most suitable for the industrial scale production of (1-alkylindol-3-ylmethyl) benzoic acid derivatives, in particular Zafirlukast and analogs. Further, this process is most suitable for the generation of a large library of intermediates and analogues of the Zafirlukast. The first step of this process involves Sonogashira coupling wherein diverse functionalization is possible with the use of substrate screening methods. While, these Sonogashira products could be utilized to generate yet another library of indole derivatives employing $Sp^3$C—H bond activation strategy. Further, the amidation and reductive amidation sequences could be performed by using a variety of substrate partners to generate and build a vast library of Zafirlukast analogues with diverse functional modifications. All the reaction steps involve purification and systematic characterization of the individual reaction product at each stage of the process.

The present process for the preparation of (1-alkylindol-3-ylmethyl) benzoic acid derivatives, in particular Zafirlukast and analogs compound of formula I as illustrated in scheme 1 is described as follows: This process is the most convenient and simple method involving six step reaction sequence employing simple key starting materials and reaction parameters comprising of following steps:

FORMULA I

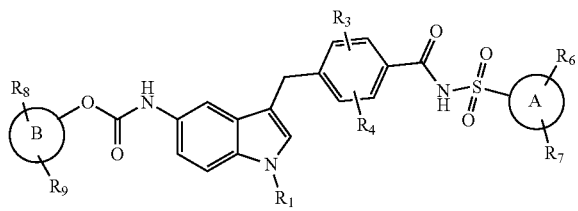

wherein ring A and B is any ring aryl, heteroaryl, cycloalkyl, fused aryl, fused alkyl or fused heteroaryl; $R_1$, $R_2$ is C1-C6 alkyl; $R_3$, $R_4$, $R_5$, $R_6$, $R_7$, $R_8$, $R_9$ is C1-12 alkyl, aryl, heteroaryl, C1-C12 cycloalkyl, heteroalkyl, thiol, H, —OR where R=H, C1-C6 alkyl, aryl or heteroaryl, $NO_2$, halogen, RNH where R=H, C1-C6 alkyl, aryl or heteroaryl; cyano, isothiocyano, isocyanate, azido, —COOR where R=H, C1-C6 alkyl, aryl or heteroaryl; —COR where R=H, C1-C6 alkyl, aryl or heteroaryl; wherein each of these groups may further be substituted with one or more substituents selected from H, OH, SH, halogen, CN, $NO_2$, C1-C4 alkyl or phenyl;

(a) Sonagashira coupling of aryl bromide compound of formula VI and aryl acetylene using palladium catalyst, copper catalyst, organic base and inorganic base in polar solvent at 70-120° C. for 5-15 hours to yield compound of formula V;

(b) oxidative cyclization of compound of formula V obtained in step (a) by $Sp^3$ C—H activation using persulfate oxidizing agent in polar solvents at 70-120° C. for 2-10 hours to yield compound of formula IV;

(c) reductive hydrogenation of compound of formula IV obtained in step (b) using catalytic hydrogenation reagent, followed by acid hydrolysis in alcoholic solvent at 25-35° C. for 2-10 hours to yield compound of formula III;

(d) amidation of acid group of the compound of formula III obtained in step (c) with sulfonamide using transition metal catalyst and anhydride in polar solvent at 25-35° C. for 1-5 hours to yield compound of formula II;

(e) reduction of nitro group of the compound of formula II obtained in step (d) using catalytic reducing reagent in polar solvent at 25-35° C. for 1-5 hours, followed by amidation with haloformate using organic base in nonpolar solvent at 25-35° C. for 2-8 hours to obtain the desired compound of formula I.

In the above process step, aryl acetylene used in step (a) is selected from

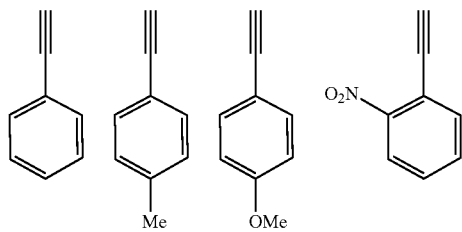

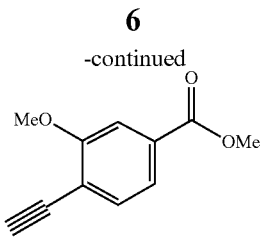

In this process, all the reaction steps were monitored by chromatography and the crude products obtained were subjected to purification using crystallization or chromatography or distillation or extraction or filtration to get the pure compounds in good yields. Further, all the resultant compounds/products were systematically characterized using various analytical and spectral methods.

EXAMPLES

Following examples are given by way of illustration and therefore should not be construed to limit the scope of the invention.

General Procedure for the Sonagashira Cross-Coupling

To a mixture of aryl bromide, compound of formula VIa-e as shown in scheme 2 (0.1 mmol), $PdCl_2$ $(PPh_3)_2$ (10 mol %), CuI (10 mol %) and $Et_3N$ (0.15 mmol) in dry DMF (4 mL) was slowly added trimethylsilyl acetylene (0.1 mmol). After complete addition the reaction mixture was stirred at 80° C. temperature for 2 h. After completion of the reaction (monitored by TLC), the reaction mixture was cooled to room temperature and $K_2CO_3$ (0.15 mmol) was added and heated to 80° C. until the silylated acetylene was disappeared (monitored by TLC). The reaction was allowed to come to room temperature followed by the addition of $PdCl_2$ $(PPh_3)_2$ (10 mol %), $Et_3N$ (0.15 mmol) and CuI (10 mol %). After stirring for 30 min at room temperature aryl halides (0.1 mmol) in DMF (2 ml) was added dropwise and the reaction mixture was heated to 80° C. for 3 h. After completion of the reaction monitored by TLC, the reaction mixture was re-cooled to room temperature and quenched with cold water (7 mL) and the solid was filtered using EtOAc (15 mL). The organic layer was washed with brine, dried over anhydrous sodium sulphate and concentrated under reduced pressure. The residue was purified by silica gel column chromatography to provide the biaryl acetylene, compound of formula Va-e as a yellow solid in three steps.

Example 1

N,N-Dimethyl-4-nitro-2-(phenylethynyl)aniline (Va)

61 mg, 56% yield; $R_f$=0.7 (silica, EtOAc:hexane=1:9); IR (neat): 3479, 3392, 2926, 2856, 1642, 1523, 1459, 1220, 1065, 772, 695 $cm^{-1}$; M.P: 87-92° C.; 1H NMR (400 MHz, $CDCl_3$): δ 8.33 (d, J=2.8 Hz, 1H), 8.03 (dd, J=9.3, 2.8 Hz, 1H), 7.52-7.48 (m, 2H), 7.38-7.33 (m, 3H), 6.76 (d, J=9.3 Hz, 1H), 3.25 (s, 6H); $^{13}C$ NMR (100 MHz, $CDCl_3$): δ 154.0, 137.4, 132.0, 129.1, 129.0, 129.0, 127.0, 122.3, 108.0, 107.2, 96.5, 83.5, 30.4, 30.0; HRMS (m/z): $[M+H]^+$ calcd. for $C_{16}H_{15}N_2O_2^+$ 267.1134, found 267.1145.

Example 2

N,N-Dimethyl-4-nitro-2-(p-tolylethynyl)aniline (Vb)

(58 mg, 51% yield; $R_f$=0.8 (silica, EtOAc:hexane=1:9); IR (neat): 2954, 2854, 2209, 1597, 1511, 1444, 1323, 1269, 1079, 906, 820, 772, 750 cm$^{-1}$; M.P: 98-103° C.; 1H NMR (400 MHz, CDCl$_3$): δ 8.32 (d, J=2.8 Hz, 1H), 8.02 (dd, J=9.3, 2.8 Hz, 1H), 7.40 (d, J=8.1 Hz, 2H), 7.17 (d, J=7.9 Hz, 2H), 6.75 (d, J=9.3 Hz, 1H), 3.24 (s, 6H), 2.38 (s, 3H); $^{13}$C NMR (100 MHz, CDCl$_3$): δ 158.0, 139.1, 139.0, 131.4, 131.2, 129.5, 125.1, 120.1, 115.0, 111.1, 96.0, 87.2, 43.0, 22.0; HRMS (m/z): [M+H]$^+$ calcd. for C$_{17}$H$_{17}$N$_2$O$_2$$^+$ 281.1290, found 281.1302.

Example 3

N,N-Dimethyl-4-nitro-2-((2-nitrophenyl)ethynyl)aniline (Vc)

(63 mg, 49% yield; R$_f$=0.8 (silica, EtOAc:hexane=1:9); IR (neat): 3393, 2922, 2854, 1624, 1530, 1444, 1343, 1220, 1020, 898, 772, 670 cm$^{-1}$; M.P: 172-177° C.; 1H NMR (400 MHz, CDCl$_3$): δ 8.41 (d, J=2.8 Hz, 1H), 8.13 (dd, J=8.3, 1.0 Hz, 1H), 8.08 (dd, J=9.4, 2.8 Hz, 1H), 7.73 (dd, J=7.8, 1.4 Hz, 1H), 7.64 (td, J=7.6, 1.2 Hz, 1H), 7.52-7.47 (m, 1H), 6.78 (d, J=9.4 Hz, 1H), 3.30 (s, 6H); $^{13}$C NMR (100 MHz, CDCl$_3$): δ 135.0, 133.1, 133.0, 129.0, 126.0, 125.0, 122.2, 122.0, 115.0, 43.0, 30.0; HRMS (m/z): [M+H]$^+$ calcd. for C$_{16}$H$_{14}$N$_3$O$_4$$^+$ 312.1023, found 312.1027.

Example 4

2-((4-Methoxyphenyl)ethynyl)-N,N-dimethyl-4-nitroaniline (Vd)

(89 mg, 73% yield; R$_f$=0.7 (silica, EtOAc:hexane=1:9); IR (neat): 3423, 3394, 2928, 2858, 1606, 1514, 1416, 1328, 1257, 1175, 1061, 805, 772, 675 cm$^{-1}$; M.P: 143-148° C.; 1H NMR (400 MHz, CDCl$_3$): δ 8.32 (d, J=2.8 Hz, 1H), 8.03 (dd, J=9.3, 2.8 Hz, 1H), 7.44 (tt, J=5.4, 2.7 Hz, 2H), 6.92-6.87 (m, 2H), 6.77 (d, J=9.3 Hz, 1H), 3.84 (s, 3H), 3.24 (s, 6H); $^{13}$C NMR (100 MHz, CDCl$_3$): δ 160.0, 157.5, 139.0, 133.0, 131.1, 131.0, 126.1, 125.0, 115.0, 114.2, 95.5, 86.3, 55.4, 43.0, 30.0; HRMS (m/z): [M+H]$^+$ calcd. for C$_{17}$H$_{17}$N$_2$O$_3$$^+$ 297.1239, found 297.1232.

Example 5

Methyl 4-((2-(dimethylamino)-5-nitrophenyl)ethynyl)-3-methoxybenzoate (Ve)

To a mixture of aryl bromide VIe (3.0 g, 10.27 mmol), PdCl$_2$(PPh$_3$)$_2$ (72 mg, 10 mol %), CuI (20 mg, 10 mol %) and Et$_3$N (2.2 mL, 15.41 mmol) in dry DMF (30 mL) after 30 min was slowly added aryl acetylene (1.95 g, 10.27 mmol). Then the reaction mixture was heated at 80° C. for 2 h, and monitored by by TLC, after completion, the reaction was quenched by the addition of cold water (50 ml) and the resulting mixture was extracted with EtOAc (3×30 mL). The organic phases were dried over anhydrous sodium sulphate, and the solvent was evaporated under reduced pressure. The residue was purified by silica gel column chromatography to give pure methyl 4-((2-(dimethyl amino)-5-nitrophenyl) ethynyl)-3-methoxybenzoate Ve (3.2 g, 89%). as a yellow solid; R$_f$=0.7 (silica, EtOAc:hexane=3:7); IR (neat): 3476, 3226, 2951, 2925, 2850, 1723, 1622, 1582, 1435, 1293, 1108, 767 cm$^{-1}$;
M.P.=152-156° C.; $^1$H NMR (500 MHz, CDCl$_3$): δ 8.38 (d, J=2.8 Hz, 1H), 8.05 (dd, J=9.3, 2.8 Hz, 1H), 7.64 (dd, J=7.9, 1.3 Hz, 1H), 7.57 (d, J=1.0 Hz, 1H), 7.51 (d, J=7.9 Hz, 1H), 6.76 (d, J=9.4 Hz, 1H), 3.96 (s, 3H), 3.94 (s, 3H), 3.29 (s, 6H); $^{13}$C NMR (125 MHz, CDCl$_3$): δ 167.0, 160.1, 157.4, 138.5, 133.0, 132.0, 131.2, 125.5, 122.0, 117.2, 115.0, 111.4, 110.1, 94.5, 91.3, 56.1, 52.5, 43.0; HRMS (m/z): [M+H]$^+$ calcd. for C$_{19}$H$_{19}$N$_2$O$_5$$^+$ 355.1294, found 355.1299.

General Procedure for the Preparation of 3-aryl indole (formula IVa-e)

To a stirred solution of Sonogashira coupling product, compound of formula Va-e (0.1 mmol) in DMSO (3 mL) was added Na$_2$S$_2$O$_8$ (0.3 mmol), the resultant mixture was put into a pre-heated oil bath 80° C. for 5 h. After completion of the reaction monitored by TLC, The resultant reaction mixture was quenched with water (5 mL) and the product was extracted with ethyl acetate (2×5 mL). The organic phase was dried over anhydrous sodium sulphate and concentrated under reduced pressure. The residue was purified by silica gel column chromatography to give 3-aroyl indole product, compound of formula IVa-e as yellow solid.

Example 6

(1-Methyl-5-nitro-1H-indol-3-yl)(phenyl)methanone (IVa)

71 mg, 68% yield; R$_f$=0.5 (silica, EtOAc:hexane=1:9); IR (neat): 3485, 2954, 2926, 2854, 1726, 1634, 1459, 1220, 894, 772, 688 cm$^{-1}$; M.P: 134-139° C.; $^1$H NMR (400 MHz, CDCl$_3$): δ 8.29 (d, J=2.6 Hz, 1H), 8.15 (dd, J=9.2, 2.6 Hz, 1H), 7.57-7.51 (m, 2H), 7.42-7.36 (m, 3H), 6.58 (d, J=9.2 Hz, 1H), 5.47 (s, 1H), 3.05 (d, J=5.2 Hz, 3H); $^{13}$C NMR (100 MHz, CDCl$_3$) δ 158.0, 139.0, 131.5, 131.3, 129.0, 127.0, 125.2, 123.1, 115.0, 111.0, 95.5, 88.0, 43.0; HRMS (m/z): [M+H]$^+$ calcd. for C$_{16}$H$_{13}$N$_2$O$_2$$^+$ 281.1690, found 281.1702.

Example 7

(1-Methyl-5-nitro-1H-indol-3-yl)(p-tolyl)methanone (IVb)

75 mg, 71%) yield; R$_f$=0.6 (silica, EtOAc:hexane=1:9); IR (neat): 2954, 2854, 2209, 1597, 1511, 1444, 1323, 1269, 1079, 906, 820, 772, 750 cm$^{-1}$; M.P: 113-118° C.; $^1$H NMR (500 MHz, CDCl$_3$): δ 8.58 (d, J=2.2 Hz, 1H), 8.15 (dd, J=9.0, 2.2 Hz, 1H), 7.42-7.39 (m, 2H), 7.36 (d, J=9.0 Hz, 1H), 7.32 (d, J=7.8 Hz, 2H), 6.69 (d, J=0.7 Hz, 1H), 3.79 (s, 3H), 2.45 (s, 3H); $^{13}$C NMR (125 MHz, CDCl$_3$): δ 145.1, 142.0, 141.1, 139.0, 130.0, 129.4, 129.0, 127.3, 118.0, 117.3, 109.5, 104.0, 32.0, 21.5; HRMS (m/z): [M+H]$^+$ calcd. for C$_{17}$H$_{15}$N$_2$O$_3$$^+$ 295.1083, found 295.1084.

Example 8

(1-methyl-5-nitro-1H-indol-3-yl)(2-nitrophenyl)methanone (IVc)

9 mg, 91% yield; R$_f$ 0.6 (silica, EtOAc:hexane=2:8); IR (neat): 3423, 3098, 2946, 1740, 1614, 1577, 1524, 1326, 1142, 1068, 855, 756, 670 cm$^{-1}$; M.P: 187-192° C.; $^1$H NMR (500 MHz, CDCl$_3$): δ 8.58 (d, J=2.2 Hz, 1H), 8.19-8.14 (m, 2H), 7.77 (td, J=7.5, 1.3 Hz, 1H), 7.70 (td, J=7.9, 1.5 Hz, 1H), 7.56 (dd, J=7.5, 1.5 Hz, 1H), 7.38 (d, J=9.1 Hz, 1H), 6.66 (d, J=0.6 Hz, 1H), 3.60 (s, 3H); $^{13}$C NMR (101 MHz, CDCl$_3$): δ 149.5, 142.1, 140.4, 139.4, 134.0, 133.3, 131.0, 127.0, 127.0, 125.0, 118.1, 118.0, 110.0, 105.0, 31.2; HRMS (m/z): [M+H]$^+$ calcd. for C$_{16}$H$_{11}$N$_3$O$_5$$^+$ 326.1489, found 598.1474.

Example 9

(4-methoxyphenyl)(1-methyl-5-nitro-1H-indol-3-yl) methanone (IVd)

77 mg, 73% yield; $R_f$=0.5 (silica, EtOAc:hexane=3:7); IR (neat): 3415, 2928, 2838, 1738, 1627, 1534, 1416, 1318, 1219, 894, 772, 685 cm$^{-1}$; M.P: 142-147° C.; $^1$H NMR (400 MHz, CDCl$_3$): δ 9.25 (d, J=1.9 Hz, 1H), 8.22 (dd, J=9.0, 1.5 Hz, 1H), 7.85 (t, J=5.5 Hz, 2H), 7.69 (s, 1H), 7.41 (d, J=9.0 Hz, 1H), 7.02-6.98 (m, 2H), 3.93 (s, 3H), 3.90 (s, 3H); $^{13}$C NMR (101 MHz, CDCl$_3$) δ 189.0, 163.0, 144.0, 140.2, 139.1, 132.5, 131.1, 121.0, 120.0, 119.1, 117.5, 114.0, 110.0, 57.0, 34.1; HRMS (m/z): [M+H]$^+$ calcd. for $C_{17}H_{15}N_2O_4^+$ 311.1032, found 311.1039.

Example 10

Methyl 3-methoxy-4-(1-methyl-5-nitro-1H-indole-3-carbonyl) benzoate (IVe)

To a stirred solution of methyl 4-((2-(dimethyl amino)-5-nitrophenyl)ethynyl)-3-methoxybenzoate (Ve) (3.0 g, 8.47 mmol) in dry DMSO (50 mL) was added Na$_2$S$_2$O$_8$ (6.05 g, 25.42 mmol), The resultant mixture was put into a preheated oil bath (80° C.) for 5 h. The resultant reaction mixture was quenched with water (60 mL) and the product was extracted with ethyl acetate (2×50 mL). The organic phase was dried over anhydrous sodium sulphate and concentrated under reduced pressure. The residue was purified by silica gel column chromatography to give methyl 3-methoxy-4-(1-methyl-5-nitro-1H-indole-3-carbonyl) benzoate (2.75 g, 88%) as a yellow solid; $R_f$=0.5 (silica, EtOAc:hexane=4:6); IR (neat): 2924, 2854, 1724, 1634, 1527, 1464, 1371, 1293, 1232, 1142, 1026, 952, 770 cm$^{-1}$; M.P.=197-202° C.; $^1$H NMR (400 MHz, CDCl$_3$): δ 9.29 (d, J=2.2 Hz, 1H), 8.23 (dd, J=9.0, 2.3 Hz, 1H), 7.73 (dd, J=7.7, 1.4 Hz, 1H), 7.69 (d, J=1.2 Hz, 1H), 7.45 (d, J=5.6 Hz, 1H), 7.42 (d, J=1.0 Hz, 1H), 7.38 (d, J=17.6 Hz, 1H), 3.97 (s, 3H), 3.87 (s, 3H), 3.85 (s, 3H).
$^{13}$C NMR (100 MHz, CDCl$_3$): δ 189.0, 166.5, 157.0, 144.3, 141.0, 140.4, 134.3, 133.0, 129.0, 126.0, 122.0, 120.0, 119.4, 118.5, 113.0, 110.1, 56.2, 53.0, 34.2; HRMS (m/z): [M+H]$^+$ calcd. for $C_{19}H_{17}N_2O_6^+$ 369.1087, found 369.1085.

Example 11

3-Methoxy-4-(1-methyl-5-nitro-1H-indole-3-carbonyl) benzoic acid (IIIe)

To a stirred solution of compound IVe (2.0 g, 5.43 mmol) in MeOH (20 mL) was added 10% Pd—C (0.2 g, 10 mol %) and conc. HCl (25 µl) sequentially. The flask was evacuated and pressurized with H$_2$ (balloon) and the reaction mixture was stirred for 6 h. After completion of reaction, The solvent was removed under reduced pressure and the pH value of the reaction mixture was adjusted to 2 with aq. HCl (2.0 M). The reaction mixture was filtered using diethyl ether and dried over anhydrous sodium sulphate. The organic layer was concentrated under reduced pressure and purified by column chromatography to give compound of formula III (1.4 g, 76%) as a yellow solid; $R_f$=0.5 (silica, EtOAc:hexane=7:3); IR (neat): 3417, 2951, 2852, 1725, 1622, 1661, 1583, 1435, 1293, 1047, 995, 825, 769 cm$^{-1}$; M.P.=162-187° C.; 1H NMR (400 MHz, DMSO-d$_6$): δ 8.51 (d, J=2.2 Hz, 1H), 8.02 (dd, J=9.1, 2.3 Hz, 1H), 7.59 (d, J=9.1 Hz, 1H), 7.50-7.45 (m, 2H), 7.36 (s, 1H), 7.25 (d, J=7.8 Hz, 1H), 4.11 (s, 2H), 3.91 (s, 3H), 3.81 (s, 3H); $^{13}$C NMR (100 MHz, DMSO-d$_6$): δ 167.2, 157.0, 140.3, 139.4, 134.1, 132.0, 130.1, 130.0, 126.5, 122.0, 116.4, 116.0, 115.3, 111.0, 110.3, 55.5, 33.0, 24.4; HRMS (m/z): [M+H]$^-$ calcd. for $C_{18}H_{15}N_2O_5^+$ 339.0981, found 339.0967.

Example 12

3-Methoxy-4-(1-methyl-5-nitro-1H-indole-3-carbonyl)-N-(o-tolylsulfonyl) benzamide (IIe)

To a stirred solution of anhydrous ZnCl$_2$ (2 mg, 30 mol %) in anhydrous dichloromethane (2 ml), carboxylic acid compound of formula IIIe (300 mg, 0.88 mmol) was added followed by the addition of benzoic anhydride (0.12 ml, 1.05 mmol) under a nitrogen atmosphere at room temperature. After 10 min, a solution of sulphonamide (16 mg, 0.88 mmol) in CH$_2$Cl$_2$ (1 ml) was added dropwise and the resulting reaction mixture was stirred at room temperature for 2 h. After completion, the reaction quenched with water (5 ml) and the mixture was extracted with CHCl$_3$ (2×10 mL) then the organic layer was washed with brine and the combined organic layer were dried over sodium sulphate and evaporated under reduced pressure. The crude compound was purified by column chromatography to afford compound of formula II (406 mg, 92%) as a yellow solid.
$R_f$=0.5 (silica, EtOAc:hexane=8:2); IR (neat): 3479, 2925, 2850, 1723, 1622, 1582, 1435, 1293, 1108, 767, 671 cm$^{-1}$; M.P.=152-156° C.; $^1$H NMR (400 MHz, CDCl$_3$): δ 9.43 (s, 1H), 8.51 (d, J=2.2 Hz, 1H), 8.25 (dd, J=8.0, 1.1 Hz, 1H), 8.10 (dd, J=9.1, 2.2 Hz, 1H), 7.52 (td, J=7.5, 1.2 Hz, 1H), 7.40 (dd, J=13.9, 5.9 Hz, 2H), 7.31-7.26 (m, 3H), 7.14 (d, J=7.8 Hz, 1H), 6.92 (s, 1H), 4.10 (s, 2H), 3.88 (s, 3H), 3.78 (s, 3H), 2.68 (s, 3H); $^{13}$C NMR (100 MHz, CDCl$_3$): δ 164.2, 157.7, 141.4, 140.0, 138.0, 137.0, 136.0, 134.2, 133.0, 132.0, 130.5, 130.4, 130.1, 127.2, 127.0, 120.0, 117.5, 117.0, 116.0, 110.1, 109.3, 56.2; HRMS (m/z): [M+Na]$^+$ calcd. for $C_{25}H_{23}N_3O_6S^+$ 516.1988, found 516.1975.

Example 13

Cyclopentyl (3-(2-methoxy-4-((o-tolylsulfonyl)carbamoyl)benzyl)-1-methyl-1H-indol-5-yl)carbamate (Zafirlukast) (I)

A solution of N-{3-methyl-4-[(N-methyl-5-nitro-1H-3-indolyl) methyl benzoyl}-2-methyl-1-benzenesulfonamide, compound of formula II (100 mg, 0.20 mmol) in MeOH (2 mL), and Raney-nickel (2 mg, 30 mol %) was placed under hydrogen pressure at room temperature for 2 h. The reaction mass was filtered through a celite bed, and the catalyst was washed with diethyl ether (2×10 mL). The combined filtrates were concentrated under reduced pressure and dried using height vacuo for 1 h. The obtained residue and N-methyl morphine (26 µl, 0.24 mmol) in CH$_2$Cl$_2$ (2 ml) was slowly added cyclopentyl chloroformate (25 µl, 0.20 mmol) at 0° C., and the resulting reaction mass was stirred at room temperature for 3 h. After completion of the reaction, the solvent was removed under reduced pressure and the solid precipitate was washed with water (5 ml) and extracted with CHCl$_3$ (10 ml) and dried over sodium sulphate and evaporated in under reduced pressure. The crude compound was purified by column chromatography to afford title product compound of formula I (102 mg, 89%) as a pale yellow solid; $R_f$=0.7 (silica, EtOAc:hexane=4:6); IR (neat): 3476, 2951, 2925, 2850, 1723, 1689, 1554, 1499, 1431, 1270, 1163, 1062, 1036, 872, 758 cm$^{-1}$; M.P.=136-141° C.; 1H NMR (500 MHz, CDCl$_3$): δ 9.18 (s, 1H), 8.26 (dd, J=8.0, 1.3 Hz, 1H), 7.51 (td, J=7.5, 1.3 Hz, 2H), 7.40 (t, J=7.5 Hz, 1H), 7.31 (d, J=1.5 Hz, 1H), 7.29 (d, J=7.5 Hz, 1H), 7.19 (d, J=8.6 Hz, 1H), 7.16 (dd, J=7.9, 1.6 Hz, 1H), 7.09 (d, J=7.9 Hz, 2H), 6.77 (s, 1H), 6.51 (s, 1H), 5.18 (ddd, J=8.9, 5.9, 2.6 Hz, 1H), 4.03 (s, 2H), 3.85 (s, 3H), 3.70 (s, 3H), 2.68 (s, 3H), 1.86 (s, 2H), 1.74 (d, J=12.6 Hz, 4H), 1.60 (s, 2H); $^{13}$C NMR (125 MHz, CDCl$_3$): δ $^{13}$C NMR (125 MHz, CDCl$_3$) δ 164.4, 158.0, 138.0, 137.0, 137.0, 134.4, 134.1, 133.0, 138.0, 130.1, 130.0, 128.4, 128.1, 127.0, 119.4, 115.2, 112.0, 110.0, 110.0, 56.0, 33.0, 33.0, 25.4, 24.0, 21.0; HRMS (m/z): [M+Na]$^+$ calcd. for $C_{31}H_{33}N_3O_6S^+$ 598.1988, found 598.1975.

Advantages of the Invention

The various advantages of the present process are given below.
1. The present process serves as a highly efficient and scalable production method for the preparation of (1-alkylindol-3-ylmethyl) benzoic acid derivatives, in particular Zafirlukast, an FDA approved drug for the treatment of asthma.
2. The advantage of the present invention is that the process could be operated by engaging all catalytic transformations and using C—H bond activation strategy.
3. Another advantage of the present invention is protection group free synthesis involving feasible reaction parameters.
4. Isolation and/or purification of the product/s is straight forward.
5. This is an attractive and economic method for the production of (1-alkylindol-3-ylmethyl) benzoic acid derivatives, in particular Zafirlukast.
6. This process could be adopted to generate a large library of process intermediates and Zafirlukast analogues.

The invention claimed is:
1. A process for the preparation of compound of formula I

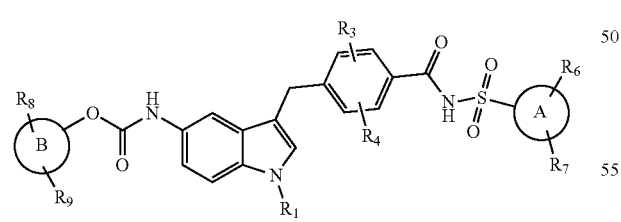

FORMULA I wherein ring A and B is any ring aryl, heteroaryl, cycloalkyl, fused aryl, fused alkyl or fused heteroaryl; R1, R2 is C1-C6 alkyl; R$_3$, R$_4$, R$_5$, R$_6$, R$_7$, R$_8$, R$_9$ is C1-12 alkyl, aryl, heteroaryl, C1-C12 cycloalkyl, heteroalkyl, thiol, H, —OR where R=H, C1-C6 alkyl, aryl or heteroaryl, NO$_2$, halogen, RNH where R=H, C1-C6 alkyl, aryl or heteroaryl; cyano, isothiocyano, isocyanate, azido, —COOR where R=H, C1-C6 alkyl, aryl or heteroaryl; —COR where R=H, C1-C6 alkyl, aryl or heteroaryl; wherein each of these groups may further be substituted with one or more substituents selected from H, OH, SH, halogen, CN, NO2, C1-C4 alkyl or phenyl; comprising the steps of:
(a) sonagashira coupling of aryl bromide compound of formula VI

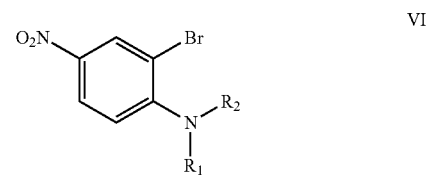

wherein R$_1$ and R$_2$ are as defined above, and aryl acetylene using palladium catalyst, copper catalyst, organic base and inorganic base in polar solvent at 70-120° C. for 5-15 hours to yield compound of formula V

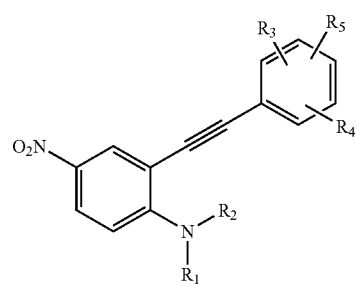

wherein R$_1$, R$_2$, R$_3$, R$_4$, R$_5$ are as defined above;
(b) oxidative cyclization of compound of formula V obtained in step (a) by Sp$^3$ C—H activation using persulfate oxidizing agent in polar solvents at 70-120° C. for 2-10 hours to yield compound of formula IV

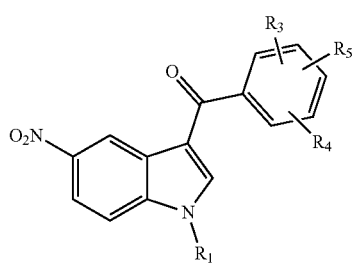

wherein R$_1$, R$_3$, R$_4$, R$_5$ are as defined above;
(c) reductive hydrogenation of compound of formula IV obtained in step (b) using catalytic hydrogenation reagent, followed by acid hydrolysis in alcoholic solvent at 25-35° C. for 2-10 hours to yield compound of formula III

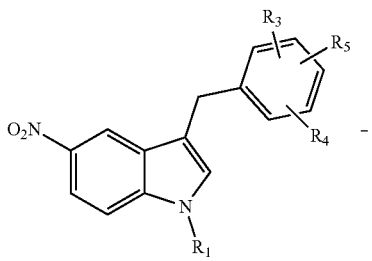

wherein $R_1$, $R_3$, $R_4$, $R_5$ are as defined above;

(d) amidation of acid group of the compound of formula III obtained in step (c) with sulfonamide using transition metal catalyst and anhydride in polar solvent at 25-35° C. for 1-5 hours to yield compound of formula II

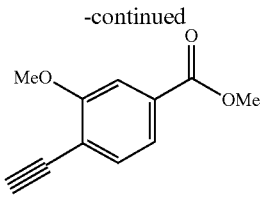

wherein $R_1$, $R_3$, $R_4$, $R_6$, $R_7$ are as defined above;

(e) reduction of nitro group of the compound of formula II obtained in step (d) using catalytic reducing reagent in polar solvent at 25-35° C. for 1-5 hours, followed by amidation with haloformate using organic base in non-polar solvent at 25-35° C. for 2-8 hours to obtain the desired compound of formula I.

2. The process as claimed in claim 1, wherein the aryl acetylene is selected from

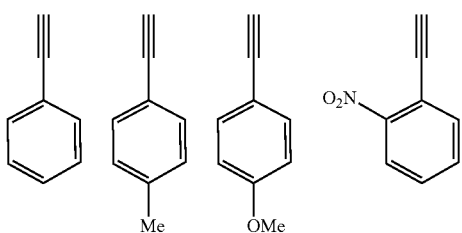

3. The process as claimed in claim 1, wherein the palladium catalyst is selected from palladium acetate, palladium chloride, tetrakis(triphenylphosphine)palladium(0), bis(triphenylphosphine)palladium(II) chloride, palladium (II) trifluoroacetate, diacetobis(triphenylphosphine)palladium(II), bis [(diphosphanyl)methyl]laminepalladium(II) dichloride, bis [(diphenylphosphanyl)methyl] aminepalladium(II)diacetate, 1,1'-dis(diphenylphosphino)ferrocene] dichloropalladium(II) or [1,1'-Bis(di-tert-butylphosphino)ferrocene]dichloropalladium(II) and the copper catalyst is selected from copper iodide, copper bromide, copper chloride or copper acetate.

4. The process as claimed in claim 1, wherein the organic base is selected from secondary amine, tertiary amine or heterocyclic amine and the inorganic base is selected from potassium carbonate, sodium carbonate, potassium bicarbonate, sodium bicarbonate, cesium carbonate, potassium phosphate, sodium phosphate or mixtures thereof.

5. The process as claimed in claim 1, wherein the polar solvent is selected from ethers, alcohols, halogenated solvents, esters, dimethylformamide, dimethylsulfoxide, acetonitrile or mixtures thereof and the non-polar solvent is selected from toluene, hexane, benzene, pentane, heptane, xylene, mesitylene or mixtures thereof.

6. The process as claimed in claim 1, wherein the persulfate is selected from sodium persulfate, potassium persulfate or ammonium persulfate.

7. The process as claimed in claim 1, wherein the catalytic hydrogenation reagent is selected from palladium on carbon or raney nickel.

8. The process as claimed in claim 1, wherein the transition metal catalyst is selected from zinc chloride, zinc bromide, zinc iodide, nickel chloride or titanium tetrachloride.

9. The process as claimed in claim 1, wherein the anhydride is selected from benzoic anhydride, acetic anhydride, phthalic anhydride or maleic anhydride.

10. The process as claimed in claim 1, wherein the haloformate is selected from chloroformate, bromoformate or iodoformate.

* * * * *